United States Patent
Bendera et al.

(10) Patent No.: US 6,555,140 B1
(45) Date of Patent: Apr. 29, 2003

(54) COMPOSITION AND METHOD FOR ENHANCING MALE FERTILITY AND LIBIDO

(76) Inventors: Richard J. Bendera, 38950 N. 54th St., Cavecreek, AZ (US) 85331; Leanna S. Wilson, 38950 N. 54th St., Cavecreek, AZ (US) 85331

( * ) Notice: Subject to any disclaimer, the term of this patent is extended or adjusted under 35 U.S.C. 154(b) by 0 days.

(21) Appl. No.: 09/869,733

(22) PCT Filed: Jan. 5, 2000

(86) PCT No.: PCT/CA00/00008

§ 371 (c)(1), (2), (4) Date: Oct. 18, 2001

(87) PCT Pub. No.: WO00/40231

PCT Pub. Date: Jul. 13, 2000

Related U.S. Application Data (60) Provisional application No. 60/114,960, filed on Jan. 5, 1999.

(51) Int. Cl.⁷ .................. A01N 59/02; A01N 31/00; C07C 211/00; A61K 35/78
(52) U.S. Cl. .................. 424/702; 564/1; 514/706; 424/725
(58) Field of Search .............. 424/195.1, 702, 424/725; 564/1; 514/706

(56) References Cited

U.S. PATENT DOCUMENTS 5,736,144 A    4/1998   Salva

FOREIGN PATENT DOCUMENTS

| CA | 2137219 | * 10/1997 |
| DE | 249 403 A | 9/1987 |
| DE | 195 12 504 A | 10/1996 |

OTHER PUBLICATIONS

Bardocz et al., "Polyamines in food–implications for growth and health", *J. Nutritional Biochemistry* 1993 4 (2):66–71.

* cited by examiner

*Primary Examiner*—Jon P. Weber
*Assistant Examiner*—Patricia Patten
(74) *Attorney, Agent, or Firm*—Licata & Tyrrell P.C.

(57) ABSTRACT

A composition for enhancing the fertility and/or libido of a male mammal is described as well as methods of enhancing fertility and libido. The composition described includes the polyamines spermine, spermidine and according to one embodiment also includes selenium.

7 Claims, 8 Drawing Sheets

COMPOSITION AND METHOD FOR ENHANCING MALE FERTILITY AND LIBIDO

This application is a 371 of Application No. PCT/CA00/00008, filed Jan. 5, 2000 which claims benefit of priority to provisional Application No. 60/114,960 filed Jan. 5, 1999.

FIELD OF THE INVENTION

The invention is in the field of male fertility and relates to a composition and method of enhancing male fertility and libido. More particularly, the invention concerns compositions comprising spermine, spermidine and/or selenium and methods of enhancing male fertility with such compositions.

BACKGROUND OF THE INVENTION

Male infertility has been increasingly recognized as a major health concern. Infertility affects an estimated 1 in 5 couples in the United States. (The Merck Manual, p. 1768 (16th Ed. 1992)). About 40 percent of infertilities are due to male deficiency. Infertility refers to the inability to conceive during the course of normal sexual activity. However, a couple is generally not regarded as infertile until they have failed to conceive after one year of unprotected intercourse. Diagnosis and treatment of infertility requires a thorough assessment of both partners (The Merck Manual, p. 1768 (16th Ed. 1992)). The male deficiency most commonly responsible for infertility is a deficiency of sperm production in quantity or quality. (McGraw-Hill Encyclopedia McGraw-Hill Encyclopedia of Science and Technology, p. 417 (6th Ed. 1987). Male infertility has been treated in a miriad of ways including increasing the intracellular synthesis of glutathione within the reproductive system (U.S. Pat. No. 5,389,657); injections of human growth hormone, (hGH) in daily doses (U.S. Pat. No. 5,250,514); or injections of testosterone analogs (U.S. Pat. No. 5,596,004).

There have also been some alternative treatments for male infertility reported. An infusion of lemongrass was reported to increase fertility in rats (Lemongrass infusions increase fertility in rats. Souza Formigoni 1986 J. Ethanopharmacol 17:65–74) and a water extract of the Chinese herb *Astragalus membranaceozis* was found to stimulate human sperm motility (*Astragalits membranaceous* stimulates human sperm motility in vitro. Hong C. Y. et al. 1992 Am. J. Chin. Med. 20:289–294).

The use of radish leaves as a medicine is well-known in the prior art. There are a number of patent documents and non-patent documents which teach the use of radish leaves to treat various ailments. Indeed it was generally known that radishes and radish leaves had a beneficial effect on health in humans. For example, U.S. Pat. No. 4,059,695 describes a type of tea that has radish leaves as one of its ingredients which acts as a general tonic for humans. As well, U.S. Pat. No. 5,498,412 describes a fermented mixture of various things including radish leaves which act as a natural antioxidant. As well, in the popular literature, a publication from 1982 describes the use of black radish in medicine (Slutomski, et al. "Black radish as a source of various phyto pharmaceuticals") (1982). Another paper describes the inhibition of mutagenicity through use of radish extract (Badrid, S. A. (1994) Cancer Letters 84:1–5). In addition, in the Encyclopedia of Herbal Medicine, radish is listed as having various health keeping properties.

U.S. Pat. No. 5,736,144 to Gideon, S., entitled "Method of Producing a Medicinal Tea For Treating Infertility in Males and For Treating Prostatitis" (filed Dec. 4, 1995 and issued Apr. 7, 1998) relates to methods for treating infertility in males and for treating prostatitis. The invention relates to a natural medicine for treating infertility in males who suffer from germinal epithelium failure and for treating prostatitis in males. In brief, the invention produces a medicinal tea from the stems and leaves of the radish plant and the preferred version of this is the species raphanus sativus. The claims are to a method of treating clinically diagnosed infertility in a mammalian male, and comprise boiling the leafy portion of radish plants of the species raphanus sativus in water for a period of time sufficient to brew a tea and having said male ingest the tea to restore fertility. The invention claimed is also a method of treating diagnosed infertility by pressing the leafy portions of radish plants to produce an extract and having the male so diagnosed ingest the extract in an amount sufficient to restore fertility. Also claimed is a method for treating microbial infections or inflamation in sexual organs of a mammalian male, comprising pressing the leafy portions of radish plants to produce an extract and having the male ingest this extract in an amount sufficient to treat the microbial infection.

However, there is no teaching in this specification of the basis for activity of the tea which is derived from the radish leaf and stem portions, nor whether such tea has any effect in any animal other than humans.

Consequently, while a variety of hormonal and other treatments have been proposed for lack of fertility in males, none have been entirely successful, and there remains a need for identifying improved and/or alternative therapies for enhancing fertility. In particular, improved methods and compositions should be effective and efficiently delivered, have minimum side effects and optionally be compatible with other hormonal treatments. The instant invention addresses this need.

SUMMARY OF THE INVENTION

The present inventors have determined that an effective amount of a composition comprising spermidine and spermine is useful in enhancing the fertility and/or libido of a male mammal. In one embodiment the composition further comprises selenium. The inventors have also developed a method of enhancing fertility of a male mammal comprising administering to the male an effective amount of a composition of the invention.

Accordingly, in one embodiment the present invention provides a composition for use in enhancing the fertility and libido of a male mammal, the composition comprising spermine and spermidine in an amount effective to enhance fertility and libido.

According to another embodiment there is provided a composition for use in enhancing the fertility and libido of a male mammal, the composition comprising spermine, spermidine, and selenium in an amount effective to enhance fertility and libido.

According to another aspect of the present invention there is provided a method of enhancing fertility and increasing libido in a male mammal. According to one embodiment there is provided a method of enhancing fertility and libido of a male mammal comprising administering to the male an effective amount of a composition comprising spermine and spermidine to enhance fertility and libido.

According to another embodiment there is provided a method of enhancing libido of a male mammal comprising administering to the male and effective amount of a composition comprising spermine, spermidine and selenium to enhance libido. According to either embodiment it is prefered that the composition is administered at least once daily.

In an embodiment of the invention according to either the method or composition where the recipient mammal is equine, a prefered composition of spermine, spermidine and selenium is about 25 mg of spernine, about 25 mg of spermidine, and about 1 mg/12 g of a composition where the 1 mg od selenium. Where spermine and spermindine are used in an equine in the absence of selenium, the spermine and spermidine are provided in the amounts of about 25 mg of spermine, about 25 mg of spermidine.

According to prefered embodiments of both the method and the composition the mammal is selected from the group of mammals consisting of equine, porcine, bovine, feline, canine, camel, sheep and human, preferably equine.

With respect to components of the composition for the composition and for the method the spermidine, spermine or selenium may be derived from green plant materials, alternatively the spermidine, spermine or selenium may be synthetically derived.

Where the the source of selenium, spermine and spermidine is from green plants, such plants are preferably selected from the group consisting of radish leaves, corn, oat, and cucumber.

In another aspect of the present invention, the inventors have also determined that a tea prepared from radish leaves when administered to horses, provides an increase in libido of the recipient horse. Accordingly, the present invention provides a composition and method for increasing the libido of a horse comprising administering an effective amount of radish tea to a horse in need thereof, where the composition comprises a tea prepared from radish leaves and stems.

Other features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE DRAWINGS

The invention will now be described in relation to the drawings in which.

DETAILED DESCRIPTION OF THE INVENTION

A chemical analysis has been performed in respect of radishes namely the chemical constituents of *raphanus sativus L* (Brassicaceae) (The Clinicians' Handbook of Natural Healing by Gary Null, Kensington Publishing, New York, 1997) Over 90 different chemicals and compounds are identified in the list of constituents. The present inventors have identified spermine, spermidine and selenium as the constituents capable of providing increased sperm count, motility and viability. Spermine and spermidine are both known as polyamines.

Polyamines are organic cations of low molecular weight which are present in both prokaryotic and eukaryotic cells. The major polyamines in mammals are putrescine, spermidine and spermine (Calandra et al. 46:209–222 (1996) Apptla).

Polyamines are ubiquitous chemicals that occur in every living cell. They fulfil an array of roles in cellular metabolism and are involved in many steps of protein, RNA and DNA synthesis, from the control and initiation of translation to the regulation of its fidelity (Dunshea and King, 73:819–828 (1995)). There is a scarcity of information on the bioavailability and mechanism of polyamine uptake by the gut and the fate of polyamines derived from the gut rumen in humans (Dunshea and King, 73:819–828). It appears that polyamines can be readily taken up from the gut rumen, and it has been suggested that this occurs by pass of diffusion (Dunshea and King, 73:819–828).

Polyamines have different patterns of tissue distribution between mammalian species and age and different hormone and environmental conditions will influence the polyamine pool (Calandra et al. 46:209–222 (1996) Apptla).

The polyamines, spermine and spermidine have been studied in connection with sperm for a considerable period of time (see for example, Colandra, R. S. et al. Physio. Pharmaco. Ther. Latinoan. 1996:46(4):209–22). However, the effect of polyamines in semen is still controversial.

Biogenic amines exist naturally in many food stuffs and vegetables such as Chinese cabbage, endive, iceberg lettuce, and radishes all of which have been found to contain varying levels of the aforementioned polyamines. However, changes in the biogenic amine content from ungerminated seeds to young plants shows a reduction in concentration of these polyamines. Further, it is not clear how such polyamines could be released from the plants aforementioned.

Both spermine and spermidine, when ingested, are transported from inside the intestine into the blood stream with only about 30% of the ingested amount being metabolically degraded. Therefore about 70% of what is ingested is metabolically available for the body to use in various cellular processes.

It has been reported that selenium provided to males as a supplement can improve sperm motility, however, it is believed that spermine, spermidine and selinium in combination has not been used to inhibit male infertility. The present inventors have found that the use of selenium in a formulation in combination with spermine and spemidine provides a suprisingly effective composition for enhancing male fertility and libido.

Accordingly the present invention is for a composition comprising spermidine and spermine in an amount effective to enhance fertility of a male mammal. In a preferred embodiment the composition comprises selenium. In still another preferred embodiment, spermine, spermidine and selenium are together in a composition in an amount effective to enhance fertility of a male mammal, particularly to increase the total sperm count and motility.

The present invention is also for a composition comprising spermidine and spermine in an amount effective to enhance libido of a male mammal. In a preferred embodiment the composition comprises selenium. In still another preferred embodiment, spermine, spermidine and selenium are together in a composition in an amount effective to enhance libido of a male mammal.

Spermine and spermidine may be the compounds as isolated from radish leaves and stems, or any other natural source, but also includes any portion of the compounds which provides the biological activity of increasing fertility in mammalian males. Also included in the meaning of the terms spermine and spermidine are any and all synthetic analogs of the naturally occurring polyamines, or biologically active portions thereof, howsoever prepared.

In another embodiment the invention provides a method of enhancing fertility and libido of a male mammal comprising administering to the male an effective amount of a composition comprising phytochemicals selected from the group consisting of: spermidine, spernine and selenium.

"Mammal" as used herein is any warm-blooded vertebrate of the class secreting milk to its young. In a preferred embodiment the mammal is selected from the group of mammals consisting of: human, horses (equine), cattle (bovine), dogs (canine), cats (feline), whales, mice, pigs (porcine) and camels.

Spermidine and spermine are derived from green plant materials. Although, it is possible to produce synthetic or recombinant spermidine, spermine and selenium, it is preferably derived from radish leaves, radish seeds, corn, oat, and cucumber, lettuce, lentil seeds, cabbage.

"Effective amount" as used herein is the amount required at dosages and for periods of time necessary to achieve the specified desired result.

Dosage Regimes

Where mice are the mammals, a dose that should produce positive results would be at least 5 ug of spermine (2.5 ug) and spermidine (2.5 ug) per day. Where the mammal is a horse, the "tea" of the invention is preferably prepared by boiling 9 g of dry material (radish leaves) per 1 liter of water, in batches of 4 liters. In the alternative a "tea" may be prepared by leaving the dry material in cold solution overnight. In either case, the greenish-brown "tea" was refrigerated (up to 9 days) until administered to the horses. Each horse may be administered 1 liter with a morning feeding and 1 liter with an evening feeding, for a total of 2 liters per day.

A person skilled in the art, upon reading this description, would appreciate that the dosages of the active substances of the compositions of the invention can vary depending on many factors such as pharmacodynamic characteristics of the particular substance, and its mode and routes of administration; source of substance; age, health, and weight of the patient, nature and extent of symptoms; kind of concurrent treatment; frequency of treatment; and the effect desired.

The compositions of the present invention when administering spermine, spermidine and/or selenium preferably contain suitable pharmaceutical carriers or diluents as appropriate. Suitable pharmaceutical carriers and methods of preparing pharmaceutical dosage forms are described in *Remington's Pharmaceutical Sciences*, Mack Publishing Company, Vetinary Drug Handbook, Donald C. Plum, University of Minnesota, and Canadian Compendium of Vetinary Products, Canadian Animal Health Institute, 6th Ed., North American Compendium Ltd., Hensal, Ontario, a standard reference in this field. Suitable pharmaceutical diluents, excipients, or carriers suitably selected with respect to the intended form of administration, that is, oral tablets, capsules, elixirs, syrups, teas, paste and the like, consistent with conventional pharmaceutical practices. Routes of administration include oral, transdermal, and injection by intravenouus, intramuscular or subcutaneous routes. A person skilled in the art would readily ascertain what a suitable pharmaceutical carrier would be.

The following non-limiting examples are illustrative of the present invention:

EXAMPLES

Example 1

Previously, (Gideon, U.S. Pat. No. 5,736,144) humans were instructed to ingest "tea" prepared from radish leaves and stems twice daily, made from a total of 3 g of dried material. In light of the present invention, this would represent a daily dose of 4500 ug of polyamine/day. The "tea" is made by placing 1.5 g of dried, broken leaf material in 1.25 cup of water. Once it comes to a boil, it is boiled for 2–3 minutes then let to cool. The active ingredients are in the aqueous portion. Based on body mass scaling it should be sufficient for a mouse to drink 0.5 ml/day of this "tea".

For mice experiments, based on this approach, a dose that should produce positive results would be 5 ug of spermine (2.5 ug) and spermindine (2.5 ug) per day. The concentrations of these compounds in a tea will be lower.

Example 2

This study illustrates that a radish leaf and stem "tea" ingested by horses is associated with an increase in sperm concentration and motility as well as libido.

Methodology

Four Standardbred stallions were used for the study. The study was conducted in accordance with the guidelines of the Canadian Council of Animal Care. Of the horses were used for testing—3 were located at the same farm in Campbellville Ontario and 1 at a farm in London Ontario.

"Tea" was prepared by boiling 9 g of dry material (radish leaves and stems)per 1 liter of water, in batches of 4 liters. The greenish-brown "tea" was refrigerated (up to 9 days) until administered to the horses. Each horse was administered 1 liter with the morning feeding and 1 liter with the evening feeding, for a total of 21/day.

Twice weekly sperm was collected using an artificial vagina and immediately analyzed for volume, sperm concentration and motility as described by Jasko (1992).

Data were analyzed using a repeated measures one-way analysis of variance. Statistical significance was accepted at $p \geq 0.05$ at a power of 80%.

Results

Figure 1:
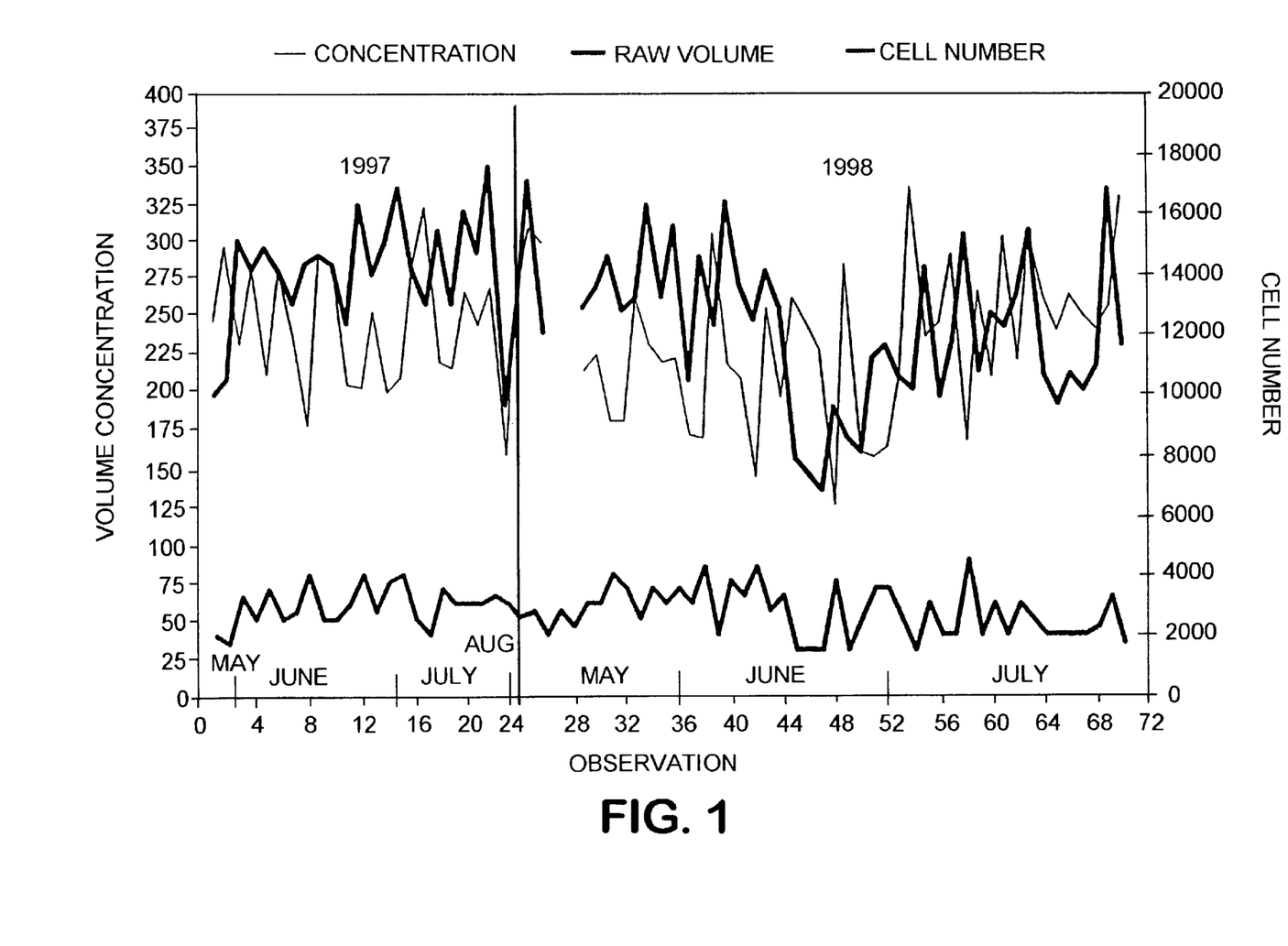
FIG. 1 is a graph illustrating the raw volume of sperm, concentration of sperm and total cell numbers for an individual horse over time.
Figure 2:
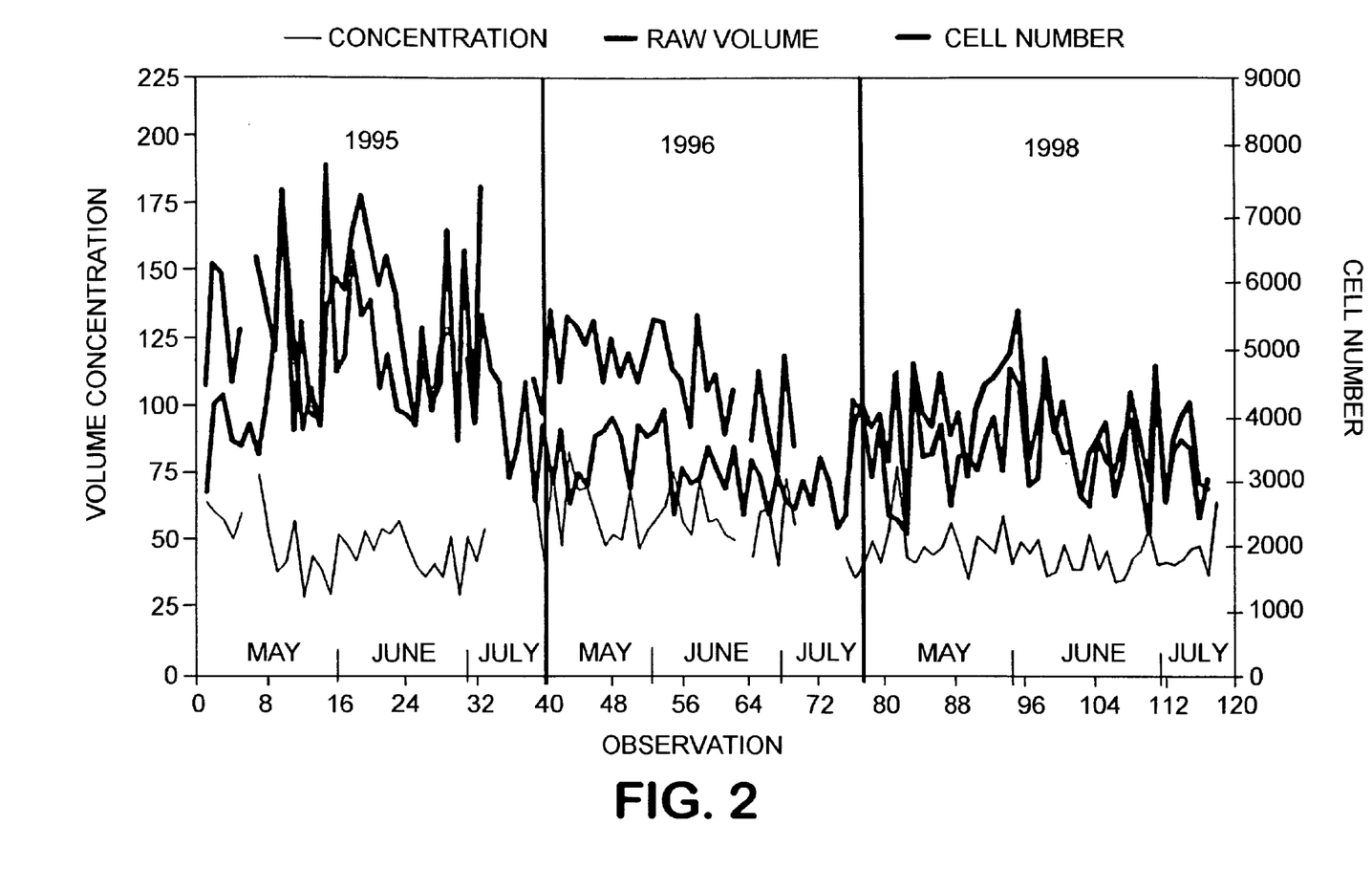
FIG. 2 is a graph illustrating the raw volume of sperm, concentration of sperm and total cell numbers for a second horse over time.
Figure 3:
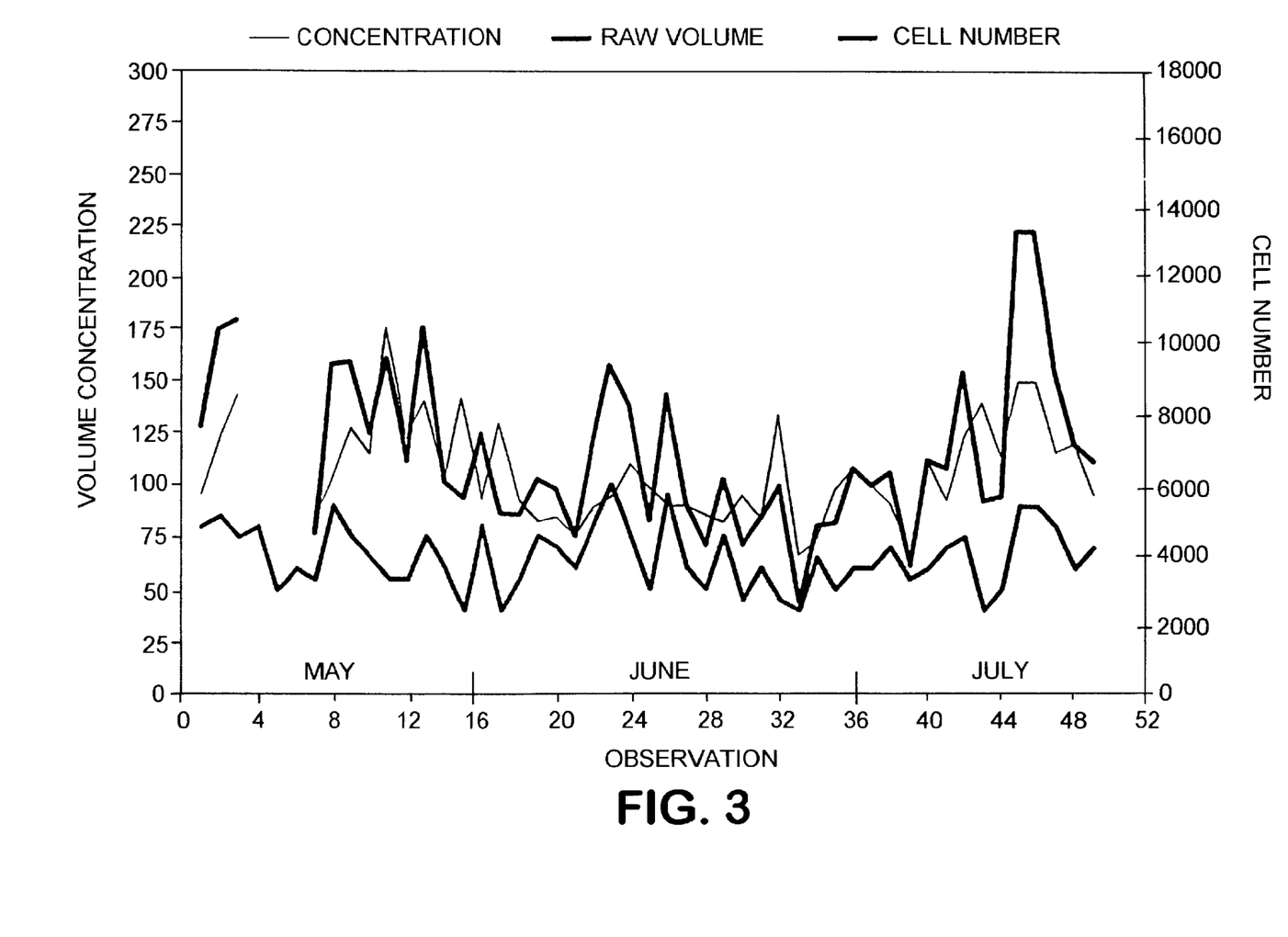
FIG. 3 is a graph illustrating the raw volume of sperm, concentration of sperm and total cell numbers for a third horse over time.
Figure 4:
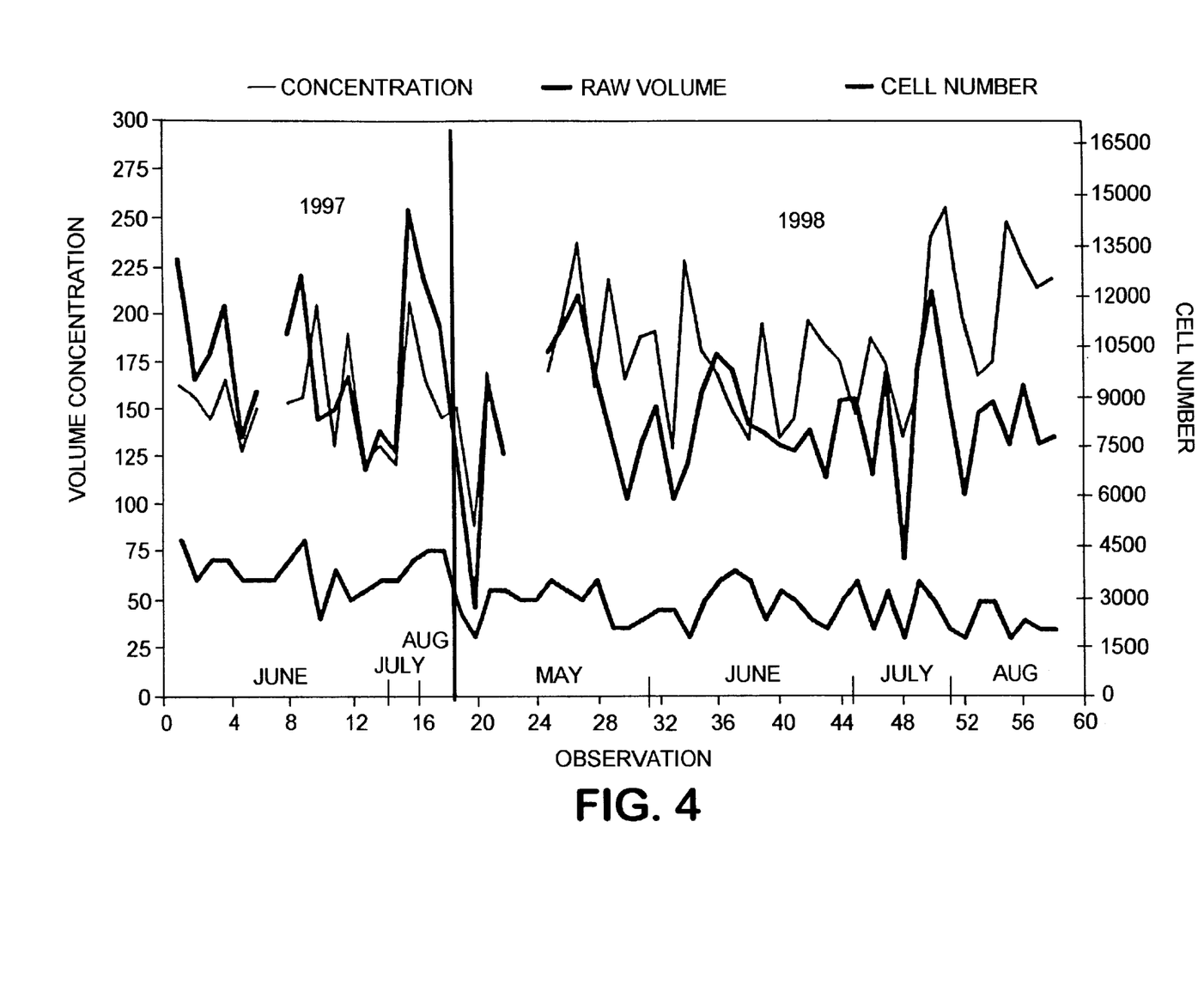
FIG. 4 is a graph illustrating the raw volume of sperm, concentration of sperm and total cell numbers for a fourth horse over time.
Figure 5:
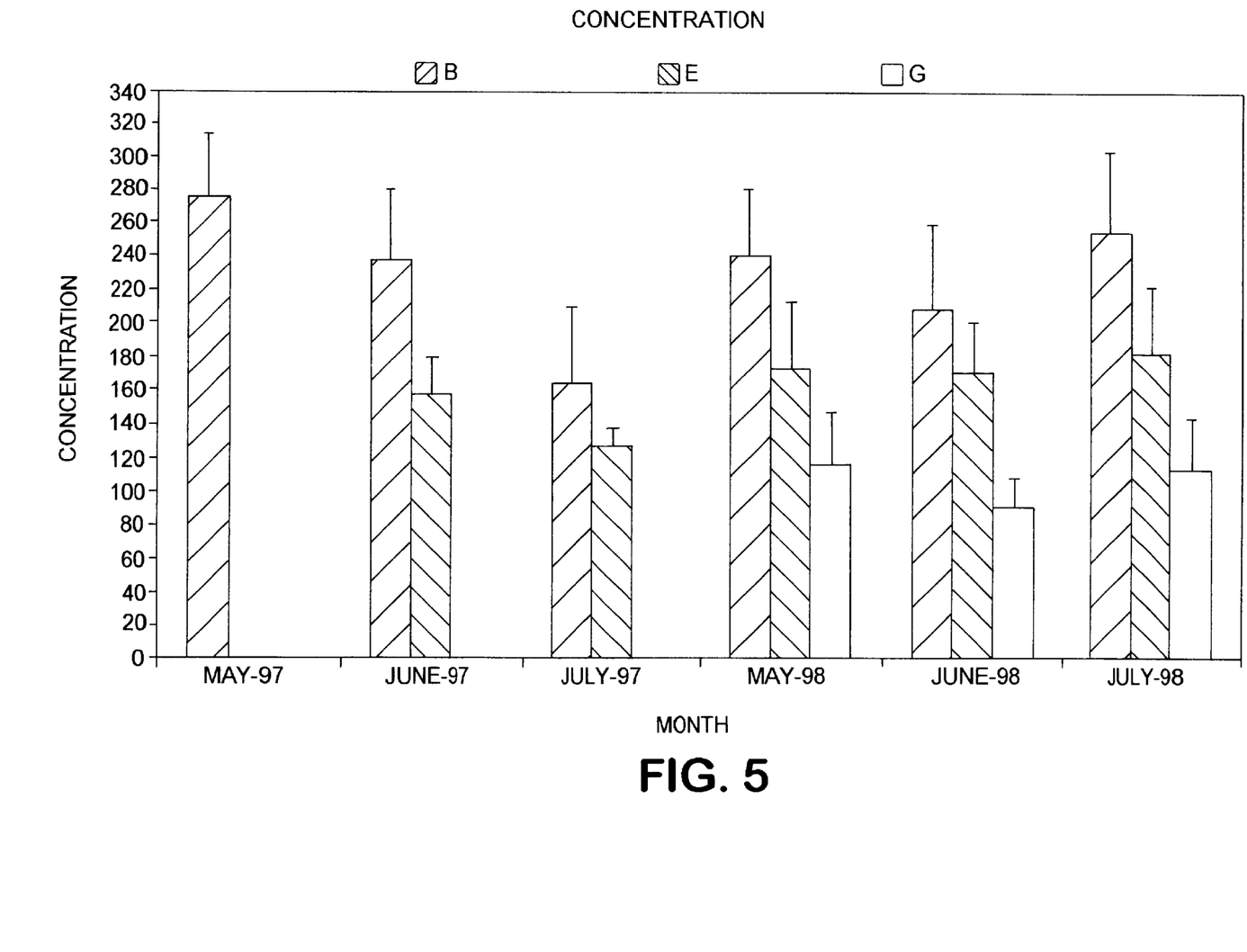
FIG. 5 is a histogram illustrating the change in concentration of sperm over a test period where (b) represents the data from the horse whose raw data is presented in FIG. 4; (e) represents the data from the horse whose raw data is presented in FIG. 1; and (g) represents the data from the horse whose raw data is presented in FIG. 3.
Figure 6:
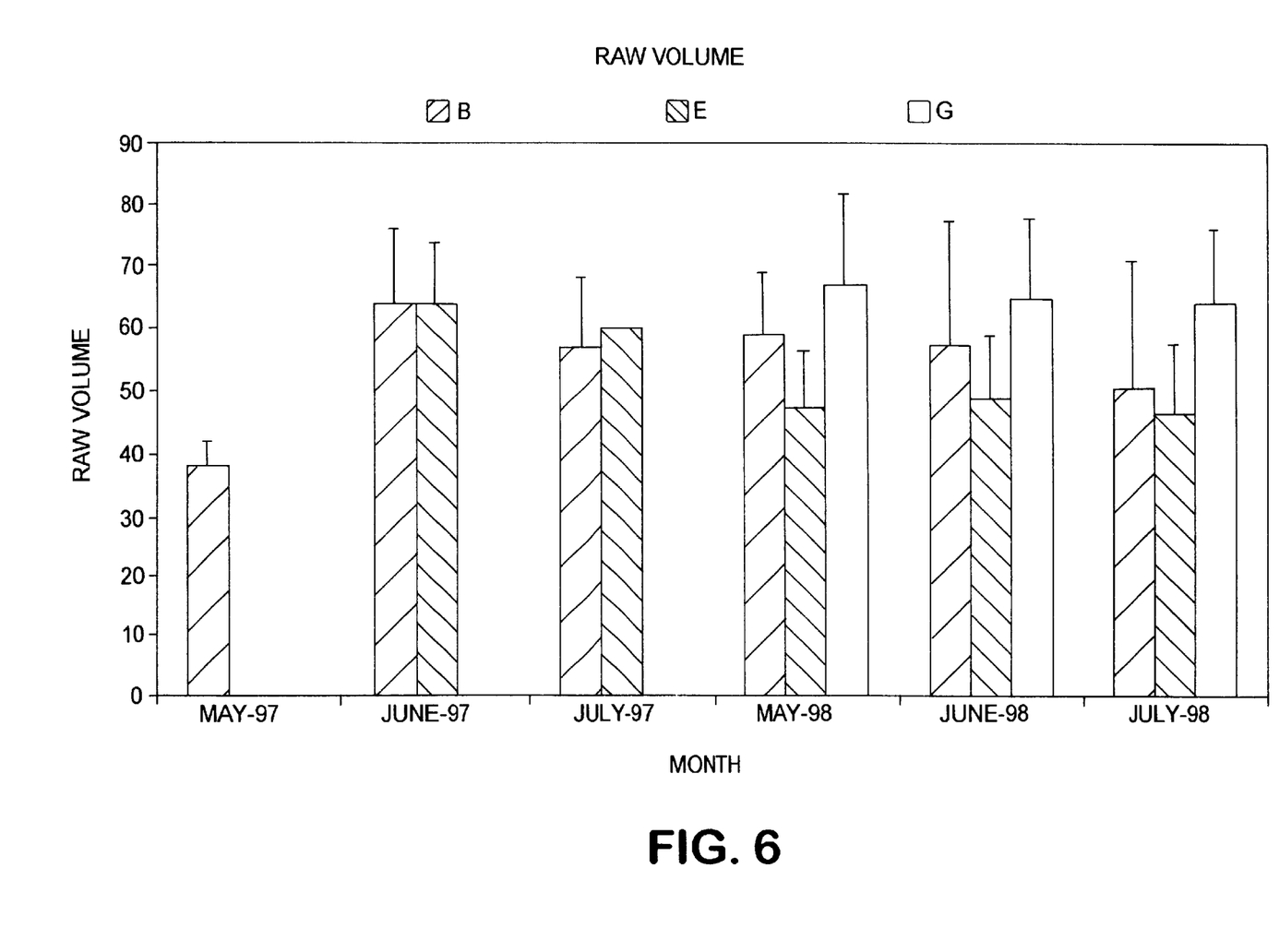
FIG. 6 is a histogram representing raw volume of sperm production where (b) represents the data from the horse whose raw data is presented in FIG. 4; (e) represents the data from the horse whose raw data is presented in FIG. 1; and (g) represents the data from the horse whose raw data is presented in FIG. 3, over a period of time.
Figure 7:
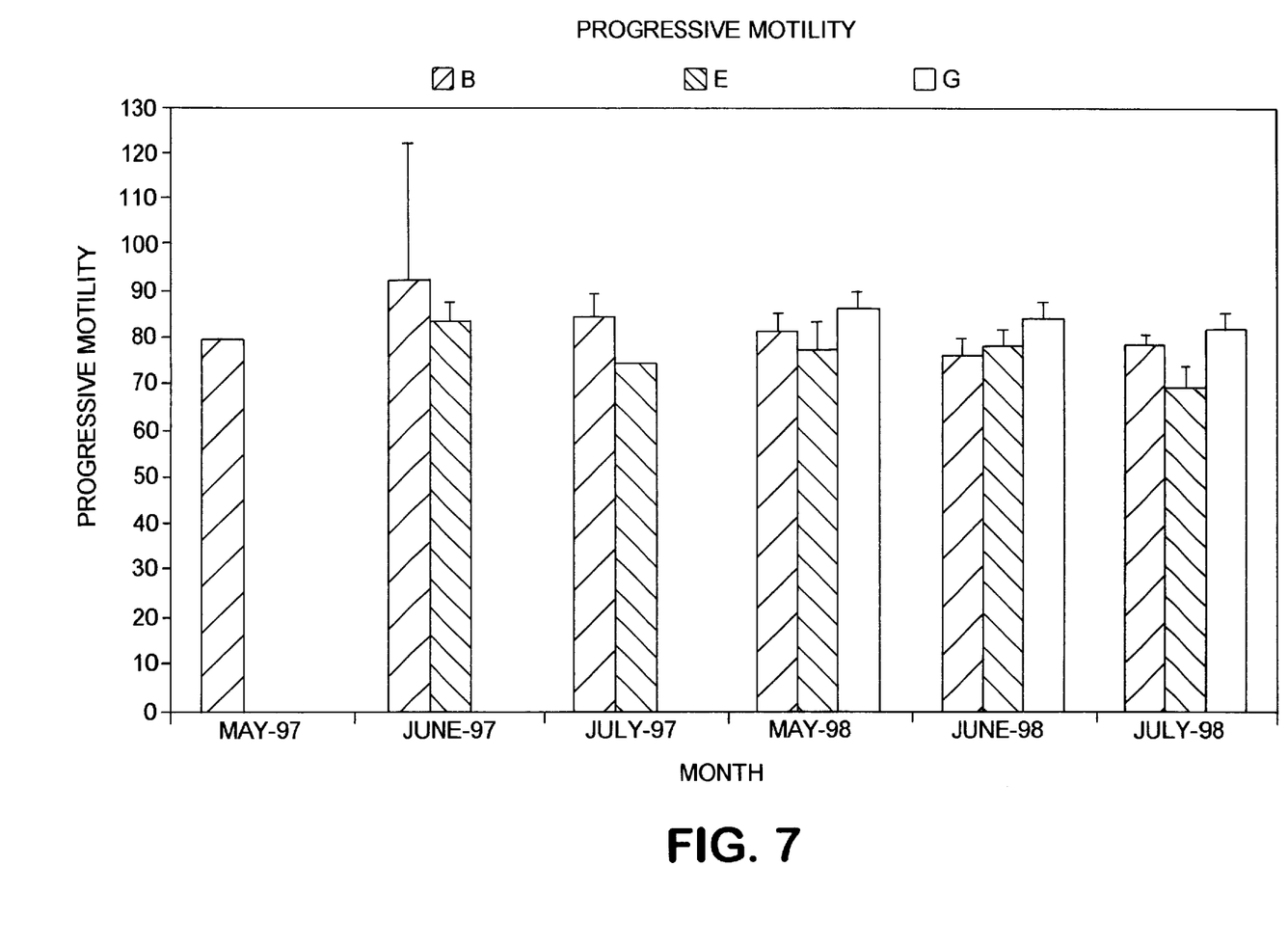
FIG. 7 is a histogram reflecting progressive motility of sperm where (b) represents the data from the horse whose raw data is presented in FIG. 4; (e) represents the data from the horse whose raw data is presented in FIG. 1; and (g) represents the data from the horse whose raw data is presented in FIG. 3.
Figure 8:
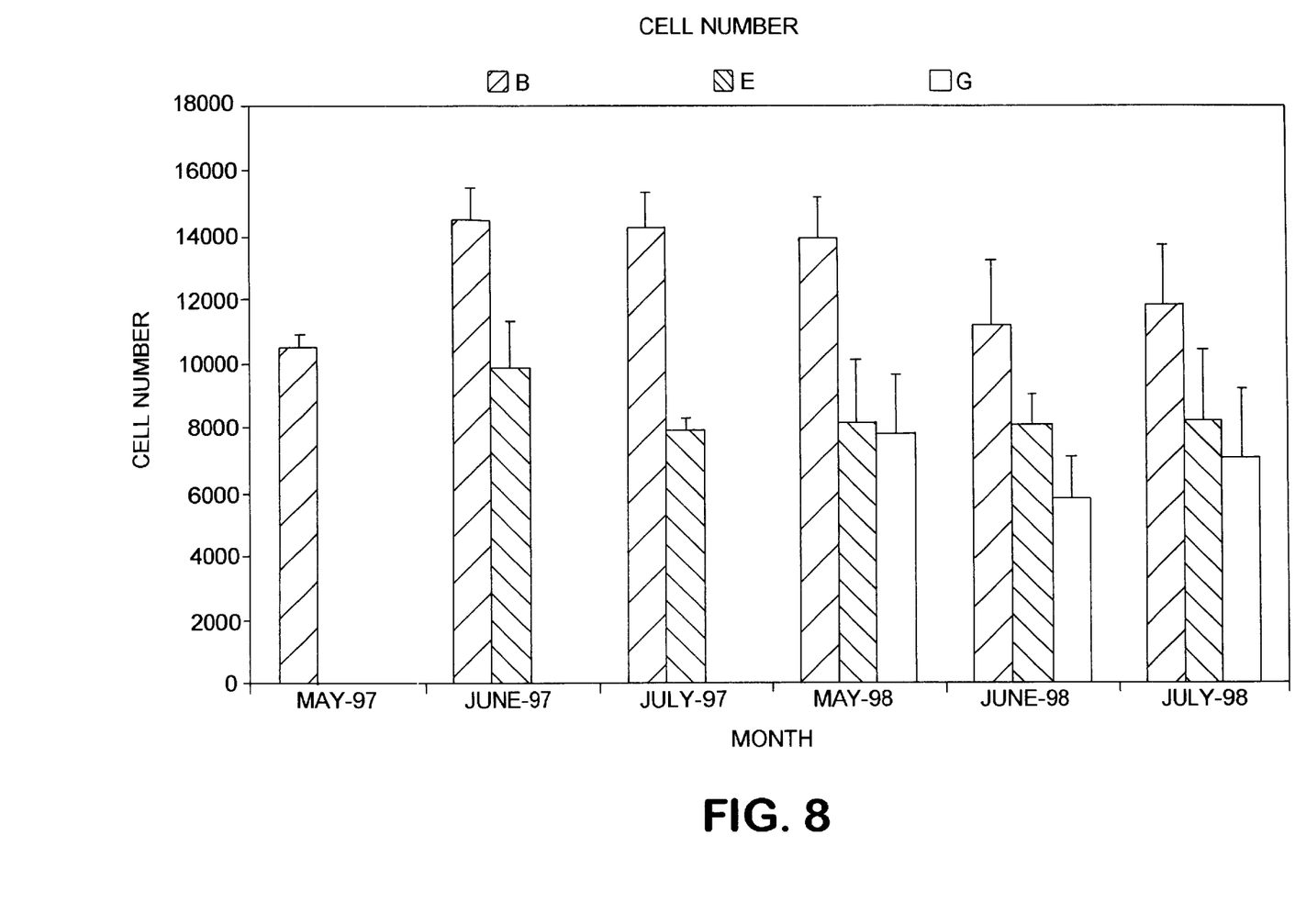
FIG. 8 is the total cell number where (b) represents the data from the horse whose raw data is presented in FIG. 4; (e) represents the data from the horse whose raw data is presented in FIG. 1; and (g) represents the data from the horse whose raw data is presented in FIG. 3.

The individual data are shown in the figures, in which FIG. 1 represents testing on horse "e", June–August 1998, with comparable data for June–August 1997, the previous year. Raw volume, concentration, and numbers of cells were recorded. NOTE: concentration & cell numbers were not available Aug. 23–Aug. 31, 1997. Referring to FIG. 2, the graph represents testing on horse "rtt" with comparable data for May–July for years 1995, 1996, & 1998. NOTE: raw volume data for 1996 not available and no data for 1997 was available. With respect to FIG. 3, this represents testing on horse "gd" for May–August 1998. No previous year data were available. Concerning FIG. 4, the data presented represent testing on horse "bi" with data for May–August 1998 compared to data from May–August 1997.

Finally, with respect to FIGS. 5–8 there is provided early/preliminary data prior to completion of June–August 1998 study on the 3 horses located at Campbellvile Ontario.

Considering the data overall, one of the horses (RTT, results in FIG. 2) had normal sperm concentration of 250±50 million/ml, while three horses (e, see FIG. 1; g, see FIG. 3, and b, see FIG. 4) had low-normal sperm concentrations of 130±30 million/ml. Sperm volume in all horses was in the normal range, although the horse with the lowest volume (g, see FIG. 3) had the highest concentration.

There was no tendency for a decrease in sperm volume, sperm concentration, and sperm motility over the three month period of tea administration for these 4 horses, indicating a possible beneficial effect for maintaining sperm quantity and volume during the period of the study. Careful examination of individual responses showed that two horses (b, FIG. 4 and g, FIG. 3) showed a tendency for increasing sperm concentration with time. Although as a group there were no statistically significant increases in sperm volume, sperm concentration, and sperm motility over the three month period of tea administration, it is important to note that the study was conducted on "normal" stallions at the end of the normal breeding season, a time when these variables may tend to decrease.

The tea was highly palatable and the horses looked forward to having it with their hay cubes. They literally drank the tea as it was being poured onto the hay cubes. There were no noticeable side effects, either beneficial or detrimental, of the tea ingestion.

There was a notable increase in libido in three of the four horses.

Discussion

The results of the study show no decrease in sperm concentration, motility and volume with time during three months of "tea" administration, at a time when these variables are expected to decrease. The lack of change may be of significance given that sperm parameters change in the non-breeding season, compared to values observed in the breeding season (Stewart and Roser 1998; Araujo et al. 1996: Magistrini et al. 1987).

This study indicates a beneficial effect for maintaining sperm count and volume during a time when horses are corning off the breeding season, and that the horses used did not have clinically low sperm concentrations.

Example 3

Studies for the evaluation of the effects of medicinal tea prepared from radish leaves (Species-raphanus sativus) for treating infertility in males using normal mice as an animal model were conducted.

| Test and Control Materials | | |
|---|---|---|
| Test Article: | | |
| Name: | Dry Radish Leaves and Stems | |
| Appearance: | Dry, crushed green leaves and stems of slight aromatic odour | |
| Control Articles: | | |
| A. | Name: | Spermidine Free Base |
| | Lot #: | 117H2620 |
| | Appearance: | White solid |
| | Solubility: | Soluble in water up to 50 mg/ml |
| | Product Supplier and Catalogue #: | Sigma Chemical Co., Cat. #S626 |
| | CAS #: | 124-20-9 |
| | Purity: | 98% (by GC) |
| | Storage Conditions: | Refrigerated (2°–8° C.) |
| B. | Name: | Spermine Free Base |
| | Lot #: | 087H2611 |
| | Appearance: | White Solid |
| | Solubility: | Soluble in water up to 50 mg/ml |
| | Product Supplier and Catalogue #: | Sigma Chemical Co., Cat. #S3256 |
| | CAS #: | 71-44-3 |
| | Purity: | >99% (by thin layer chromatography) |
| | Storage Conditions: | Refrigerated (2°–8° C.) |

Test and Control Article Preparation

Test Article ("Tea") Preparation

The "tea" is made by placing 1.5 g of dried, broken leaf material in 297 mL (1.25 cup) of water. Once it comes to a boil, it was boiled for 2–3 minutes then allow to cool. Any unused portion was stored in the refrigerator at 2–8° C. and used on subsequent days (up to 3 days).

Spermine and Spermidine Preparation

Spermine and spermidine is separately prepared (dissolved) as a 5 mg/ml w/v in water solutions. Equals amounts of spermine and spermindine solutions are then combined. The resulting solution contains 2.5 mg/ml of each compound. For this study and all subsequent studies spermine, spermidine and selenium were purchased as pure compounds either from Sigma Chemical Company or Fisher Scientific through Ukele Health Products (Blissfield, Mich.).

| Test System: | |
|---|---|
| Species: | CD-1 (Swiss Albino) mouse |
| Source: | Charles River Canada |
| Number and Sex: | 20 Male |
| Initial Age: | ~6 weeks of age |

Environment

All animals were housed in environment-controlled rooms as per "Guide for the Care and Use of Laboratory Animals", CCAC, 1993. The animal room environment throughout the study was controlled (targeted ranges: temperature 22° C.±2° C., relative humidity 30–70%) and monitored daily. The photocycle was 12 hours light and 12 hours dark.

| Basal Diet: | Certified (commercially available) Tekland Rodent Diet fed ad libitum throughout the study. |
|---|---|

-continued

Water Supply: Tap water ad libitum supplied to the cage via a water bottle.

EXPERIMENTAL DESIGN

Protocol

Normal male CD-1 mice received radish "tea" treatment over a 6 week period. Groups, dose levels and scheduling are summarized in Table 1.

TABLE 1

| Group | No. of Animals & Strain | Dose (μg/25 mouse) | Dose Volume (mL) | Route | Frequency |
|---|---|---|---|---|---|
| 1. Test (herbal Tea Extract) | 10 CD-1 | 1.5 | 0.5 mL/mouse | oral | Daily for 6 weeks |
| 2. Negative Control (Water) | 10 CD-1 | 0 | 0.5 mL/mouse | oral | Daily for 6 weeks |
| 3. Positive Control (Spermine/ Spermidine | 10 CD-1 | 2.5 μg Spermine + 2.5 μg Spermine | 0.5 mL/mouse | oral | Daily for 6 weeks |

Electroejaculation was performed in all animals, twice a week during a 6 week period in order to stimulate sperm production.

Four days before the end of the study, animals from both groups were injected subcutaneously with a marker of cell proliferation [bromodeoxyuridine (BrdU) at 50.0 mg/Kg].

At the end of the study, the animals were sacrificed by $CO_2$ exposure. The testes and epididymides were preserved in 10° buffered formaldehyde. The epididymides were processes and H&E stained. The number of spermatozoa per 40×field in 10 epididymal ducts per animal were counted. The testes were processed and stained (immunohistochemistry) using a marker specific for bromodeoxyurdine (BrdU). The number of proliferating cells per 40×field were quantified, in 10 different sites (per testes) per animal.

Any intergroup difference of the number of spermatozoa and the number of proliferating cells were assessed statistically using the student's t-test at p=0.05.

This study was conducted in compliance with the Good Laboratory Practice standards as described in the United States Food and Drug Administration, Title 21 Code of Federal Regulations Part 58, Revised Apr. 1, 1996.

Results

Significant increase in sperm count was observed in the animals tested. A decrease in motility was observed but this is greatly offset by the increase in sperm count. The results of the study are reported in Tables 2–4 below.

TABLE 2

One Way Analysis of Variance

| Group | N | Missing |
|---|---|---|
| I-Count; Rela | 10 | 0 |
| II-Count; Relati | 10 | 0 |
| III-Count; Relar | 10 | 0 |

| Group | Median | 25% | 75% |
|---|---|---|---|
| I-Count; Rela | 89.250 | 75.000 | 110.500-Tea |
| II-Count; Relati | 62.500 | 52.500 | 66.500-Placebo |
| III-Count; Relar | 72.750 | 51.000 | 88.500-Positive Control (S&S) |

The results indicate 42.8% increase in sperm count with the tea composition versus the placebo.

Although a 28% loss in motility was observed (see below), the increase in sperm count off-sets the decrease in motility.

Motility

TABLE 3

One Way Analysis of Variance

| Group | N | Missing |
|---|---|---|
| I-Motitlity % | 10 | 0 |
| II-Motitlity % | 10 | 0 |
| III-Motitlity % | 10 | 0 |

| Group | Mean | Std. Div | SEM |
|---|---|---|---|
| I-Motitlity % | 37.500 | 20.582 | 6.509-Tea |
| II-Motitlity % | 62.500 | 65.000 | 17.159 5.426-Placebo |
| III-Motitlity % | 44.000 | 27.162 | 8.589-Positive Control (S&S) |

| Source of Variation | DF | SS | MS | F | F |
|---|---|---|---|---|---|
| Between Treatments | 2 | 4131.667 | 2065.833 | 4.257 | 0.025 |
| Residual | 27 | 13102.500 | 485.278 | | |
| Total | 29 | 17334.167 | | | |

All Pairwise Multiple Comparison Procedures (Student-Newman-Keulis Method):

Comomparision for Factor

| Comparison | Diff of Means | p | q | P < 0.05 |
|---|---|---|---|---|
| II-Motility % vs I-Motility % | 27.500 | 3 | 3.948 | Yes |
| II-Motility % vs III-Motility % | 21.000 | 2 | 3.015 | Yes |
| III-Motility % vs I-Motility % | 6.500 | 2 | 0.933 | No |

The results indicate a 28% decrease in motility with the tea composition compared to placebo. A 21% decrease in motility with the spermidine/spermine composition compared to placebo was observed. No significant difference between the tea and spermidine/spermine composition with regard to motility was observed. It is expected that selenium will overcome any decrease in motility.

Variability in Larger Groups

TABLE 4

| Group Name | N | t-test Missing | Mean | Std. Dev. | SEM |
|---|---|---|---|---|---|
| Row 1 | 20 | 0 | 89,250 | 50.600 | 11.315 |
| Row 2 | 20 | 0 | 62.500 | 31.600 | 7.066 |
| Difference | 26.750 | | | | |

T=2.005 with 38 degrees of freedom. (P=0.052) 95 percent confidence interval for difference of means: −0.255 to 53.755

This calculation shows that with groups of 20 animals, with the same amount of variability observed in the above studied 3 groups of 10, statistical significance would be achieved (P=0.05).

Therefore, when considering groups of 100's and 1000's of individuals the results would be highly significant.

Example 4

The results from Examples 2 and 3 illustrate that the radish leaf "tea" of the prior art is able to achieve improvements in fertility in horses and mice. The data from Example 3 illustrates that the compounds of the present invention are able to mimic this result. A further study was conducted in mice to determine the objective effects of a spermidine/spermidine composition of the invention. This study was a blind study.

The preparations of the spermine/spermidine compositions and administration protocols were as described in Example 3.

Ten male B6D2F-1 mice were treated daily for one week prior to mating. The females used in the study were B6C3F1. The control group received water. Both male and femal mice were purchased from Harlan, Sprague, Dawley of Indianapolis Ind. The results are as shown in Table 5.

TABLE 5

| | treated donor/injected | control donor/injected |
|---|---|---|
| Group 1 | 5 (27.6)/9 (15.3) | 15 (18.5)/26 (11.0) |
| Group 2 | 5 (28.2)/9 (15.6) | 18 (18.4)/26 (13.8) |
| Group 3 | 7 (28.5)/9 (22.0) | 12 (16.0)/19 (10.0) |

Male mice in groups 1–3 were treated daily with a spermine/spermidine composition of the invention. The numbers in the table represent the number of females and embryos retrieved from the treated and the control group. For instance, taking the numbers from Group 1 and the results in the treated group: 5(27.6)/9 (15.3), the "5" refers to the total number of females from which embryos were retrieved, while the "9" refers to the total number of females collected from for this collection. The number in parenthesis following the "5" and "9" refers to the average number of embryos retrieved from the contributing females.

The results from the study are significant, showing an increase of 37.6% in the treated donor group versus the control donors. The injected comparison shows similar increases (by injection, it is meant that both control and treated groups received oral injection using a syringe).

This data, which reflects an increase in fertilization rates is likely due to increased motility of sperm in treated animals, or an increase in sperm count or a combination of both. In the light of the results obtained in the study in Example 3, it seems reasonable to conclude the increase was due to increased sperm count.

Example 5

Studies were conducted to test the effectiveness of the spermine/spermidine or spermine/spermidine/selenium composition in stallions.

Spermine/Spermidine Studies

In a first study, a composition comprising 25 mg spermine and 25 mg of spermidine and corn syrup in a total volume of 5 ml (supplied in syringes) was adminstered to five stallions one syringe dose per day, given orally, daily over a three month period. Three stallions were placed on the medication because of subfertility, and two were placed on the medication because of low libido. Libido in stallions is readily apparent when a stallion is presented to a mare, the stallion will show signs of aggression, bellow/nickering, and show signs of flaming whereby the stallion smells the mare's tail, hips, and vulva. Sometimes they role their upper lip. Penis drops down from sheath (drawing or dropping down), has an erection with the end of penis swelling. In a few seconds stallion wants to mount mare. On the other hand, horses with low or subnormal libido will just stand still showing none or few of the above signs. The sexual behaviour of the "low-libido" stallions was significantly enhanced following treatment with the composition. With respect to the three subfertile stallions, there has not been a clear improvement in semen quality or testicular function.

In a second study, using the same composition as used in the first stallions, five further stallions received the same dosage regime as in the first study. There was a significant improvement in libido in all animals tested. Further, in these stallions an increase in sperm count has been observed although motility was poor.

In a third study, two stallions with low or subnormal sexual drive were treated orally, one syringe per day, with a composition as used in the first and second studies.

Spermine/Spermidine/Selenium Studies 19 stallions were treated with 25 mg of spermine, 25 mg of spermidine, and 1 mg/12 g of a composition where the 1 mg is selenium, all masked with a vitamin supplement paste containing vitamin A, D, E and K, copper, zinc, manganese, American and Chinese ginseng, Mexican yams, and L-arginine in a 5 ml syringe. Increase in stallion libido and a return to acceptable breeding behaviour in a natural breeding program was observed with use of the composition. Also, it is noteworthy that there was an increase in sperm motility. No side or other negative effects (clinically, physiologically or other) have been observed.

Example 6

A 10 year old male airdale canine who exhibited sperm of poor quality and motility but with good libido was treated with a composition comprising 2.5 mg/ml spermine, 2.5 mg/ml spermidine in 1 liter of water. 200 ml of this was spread on the dog food once per day for 3 months. Libido remained very good throughout the study.

The results of the motility and sperm count are as follows:

TABLE 6

| Date | Sperm Count | Motility & Viability |
|---|---|---|
| May 6, 1999 | 18.9 million | Slow Movement, non movement or most 55% |

TABLE 6-continued

| Date | Sperm Count | Motility & Viability |
|---|---|---|
| May 7, 1999 | 26.6 million | Motility much improved, 60% moving |
| June 30, 1999 | 40.4 million | Motility improving |
| September 28, 1999 | 44 million | Motility very good, viability increased to 80% |

The results clearly indicate improved sperm count and motility and viability.

DISCUSSION

The foregoing examples illustrate that a composition of tye present invention including spermine, spermidine or including spermine, spermidine and selenium can result in an increase in libido and an improvement in sperm count, sperm motility, as well as improved sperm quality in a mammalian receipent. As indicated in the data provided in Example 3, an increase in the numbers of individuals tested should provide more significant results. Furthermore, these examples have been conducted at only a few dosage ranges. As will be understood by those skilled in the art, variations in the ranges will provide optimum results.

As will be readily appreciated the advantages of using the compounds spermine, spemidine and selenium or spermine and spermidine in a composition for administration instead of a tea prepared from plants containing these compounds are readily apparent: they include ease of preparation, accuracy of dosing, stability, enhanced shelf life, and ease and stability in transportation and delivery.

The methods and compositions according to the present invention have wide applicability in a variety of settings including the treatment of male infertility and depressed libido, particularly in the field of animal husbandry. Members of the equine, porcine, bovine, feline, camels, sheep and canine species prove to benefit from these compositions and methods.

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

FULL CITATIONS FOR REFERENCES REFERRED TO IN THE SPECIFICATION

Araujo, J. F., A. S. Righini, J. J. Fleury, M. C. Caldas, J. B. Costa-Neto and N. Marques. 1996. Seasonal rhythm of semen characteristics of a Brazilian breed ("mangalarga") stallion. *Chronobiology International* 13:477–485.

Jasko, D. J. 1992. Evaluation of stallion seme. *Veterinary Clinics of North America: Equine Practice* 8:129–148.

Jasko, D. J., T. V. Little, D. H. Lein and R. H. Foote. 1992. Comparison of spermatozoa movement and semen characteristics with fertility in stallions: 64 cases (1987–1988). *Journal of the American Veterinary Medical Association* 7:979–985.

Magistrini, M. P. Chanteloube and F. Palmer. 1987. Influence of season and frequency of ejaculation on production of stallion semen for freezing. *Journal of Reproduction and Fertility* (Supplement) 35: 127–133.

Stewart, B. L. and J. F. Roser, 1998. Effects of age, season, and fertility status on plasma and intratesticular immunoreactivity (IR) inhibit concentrations in stallions. *Domesticated Animal Endocrinology* 15: 129–130.

We claim:

1. A composition for enhancing the fertility and libido of a male mammal, the composition comprising spermine, spermidine, and selenium in an amount effective to enhance fertility and libido in said mammal, and wherein the spermidine or spermine are synthetically derived.

2. A composition for enhancing the fertility of a male mammal comprising spermine as a first component and spermidine as a second component both of said components present in said composition in an amount effective to enhance fertility and libido and wherein at least one of said components has been synthetically derived.

3. A method of enhancing libido of a male mammal comprising administering to the male mammal an effective amount of a composition comprising spermine, spermidine and selenium to enhance libido, wherein the mammal is canine and the composition comprises about 2.5 mg/ml spermine and 2.5 mg/ml spermidine in 1 liter of water.

4. A composition for enhancing the fertility and libido of a male mammal, the composition comprising spermine, spermidine, and selenium in an amount effective to enhance fertility and libido, and wherein the composition comprises about 25 mg of spermine, about 25 mg of spermidine, and about 1 mg of selenium per 12 g of the composition.

5. A method of enhancing libido of a male mammal comprising administering to the male mammal an effective amount of a composition comprising spermine, spermidine and selenium to enhance libido, and wherein the spermidine or spermine are synthetically derived.

6. The method of claim 5 wherein the composition is administered at least once daily.

7. A method of enhancing libido of a male mammal comprising administering to the male mammal an effective amount of a composition comprising spermine, spermidine and selenium to enhance libido, wherein the composition comprises about 25 mg of spermine, about 25 mg of spermidine, and about 1 mg of selenium per 12 g of the composition.

* * * * *